United States Patent [19]

Swartz

[11] 4,198,280
[45] Apr. 15, 1980

[54] MEMBRANE SUPPORT STRUCTURE FOR ELECTROCHEMICAL SENSING PROBE

[75] Inventor: Dorian J. Swartz, Yorba Linda, Calif.

[73] Assignee: American Hospital Supply Corporation, Evanston, Ill.

[21] Appl. No.: 970,891

[22] Filed: Dec. 19, 1978

[51] Int. Cl.² .......................................... G01N 27/46
[52] U.S. Cl. ............................................. 204/195 P
[58] Field of Search ........................ 204/195 P, 1 P; 128/2 E, 635; 324/29

[56] References Cited

U.S. PATENT DOCUMENTS

| | | | |
|---|---|---|---|
| 3,070,539 | 12/1962 | Arthur et al. | 204/195 P |
| 3,406,109 | 10/1968 | Molloy | 204/195 P |
| 3,875,037 | 4/1975 | Krull | 204/195 P |

FOREIGN PATENT DOCUMENTS 1523068  9/1969  Fed. Rep. of Germany ....... 204/195 P

*Primary Examiner*—G. L. Kaplan
*Attorney, Agent, or Firm*—Larry N. Barger

[57] ABSTRACT

A probe for monitoring gas concentration, such as oxygen, in an anesthesia respiratory therapy circuit which includes an improved membrane support structure. This structure includes an electrode supporting post having a roughened end and also interconnecting grooves and channels to insure electrolyte contact with the electrode. Also, there is a retaining member having an upstanding annular rib which uniformly presses the membrane against the electrode support.

6 Claims, 3 Drawing Figures

MEMBRANE SUPPORT STRUCTURE FOR ELECTROCHEMICAL SENSING PROBE

BACKGROUND

U.S. Pat. No. 3,826,730 describes an electrochemical sensing probe for determining oxygen concentration. This probe includes a membrane 52 held against an end of an electrode 54 by a cap 50. There have been problems insuring uniform pressure of such membrane against the electrode. If too much pressure is exerted, it is difficult for the electrolyte to reach the electrode. Conversely, if not enough pressure is exerted, electrolyte will build up at the electrode face causing excessively long response time of the probe.

In addition to the above mentioned reference, another sensing probe is described in my co-pending patent application entitled "Electrochemical Sensing Probe," filed Dec. 19, 1978, Ser. No. 970,890, which illustrates at the membrane-electrode contact area the general problem described above.

SUMMARY OF THE INVENTION

The above problems have been overcome with the present invention which includes a roughened surface on the electrode support. Preferably, an annular groove and connecting channel system is also used to insure sufficient electrolyte flow to the electrode. A retaining cap has a protruding annular section which uniformly presses the membrane against the electrode support. Thus, improved reproducability is achieved during manufacturing and assembly.

THE DRAWINGS

DETAILED DESCRIPTION

Figure 1:
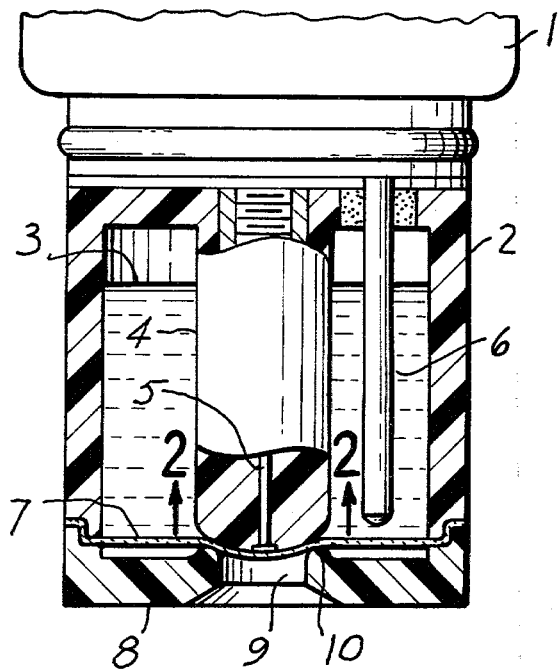
FIG. 1 is a fragmentary view showing the membrane supporting section of an electrochemical sensing probe.
Figure 2:
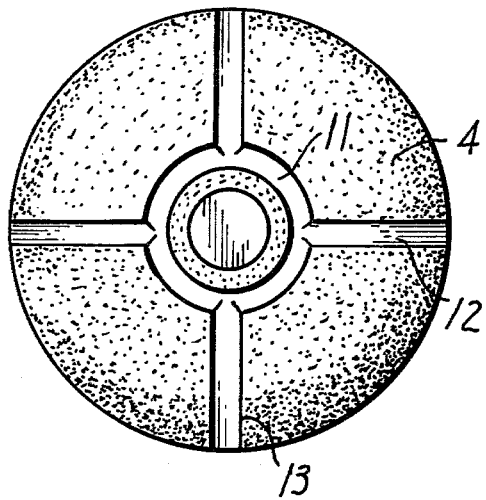
FIG. 2 is a sectional view taken along line 2—2 of FIG. 1.
Figure 3:
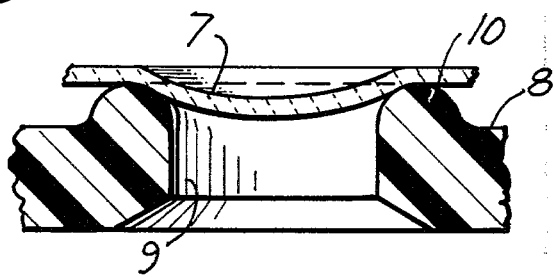
FIG. 3 is an enlarged sectional view of the retaining cap portion in contact with the membrane.

In FIG. 1, a sensing probe is shown which generally includes a connector 1, which can be reusable, joined to a disposable electrolyte housing 2. Within this housing is an electrolyte 3 contained in an annular chamber surrounding an electrode support 4 that includes in its center section an electrode 5 which can be a cathode. Anode 6 protrudes into the electrolyte 3. Retaining a membrane 7 in contact with electrode 5 is a cap 8. Cap 8 includes a central opening 9 to the atmosphere being tested. Surrounding opening 9 is an upstanding annular rib 10 with a convex cross-sectional shape in contact with membrane 7. Thus, a more predictable and uniform pressure is exerted on the membrane to hold it against electrode support 4. This provides better reproducability in manufacture and assembly.

To insure there is electrolyte contact at cathode 5, the bottom of rounded electrode support 4 is preferably roughened. This can be done by sanding the rounded end of electrode support 4 after it has been molded. Also, to insure electrolyte wetting of cathode 5, an annular groove 11 is molded into the end of electrode post 4. Groove 11 has a smaller diameter than the cap 8. Connecting the electrolyte chamber 3 with annular groove 11 are a series of radial channels, such as 12 and 13. Channels 12 and 13 extend across the pressure point at the membrane caused by annular rib 10 of the cap.

The above description has used specific embodiments to describe the invention. However, it is understood by those skilled in the art that certain modifications can be made to these embodiments without departing from the spirit and scope of the invention.

I claim:

1. An electrolyte housing for an electrochemical sensing probe that has a membrane held against an electrode support, whereby the improvement comprises: a retaining member having a protruding annular section which uniformly presses the membrane against the electrode support; said electrode support having a surface roughened to a given depth; and a lateral channel in the electrode support's end surface that is substantially deeper than the roughened surface, which channel extends laterally across the protruding annular section to prevent the blocking seal to occur between the protruding annular section and the membrane.

2. An electrolyte housing as set forth in claim 1, wherein the annular section is an upstanding rib.

3. An electrolyte housing as set forth in claim 2, wherein the rib has a convex cross-sectional area engaging the membrane.

4. An electrolyte housing as set forth in claim 1, wherein the electrolyte support has an annular groove with one or more conducting channels to the electrolyte reservoir of the housing.

5. An electrolyte housing as set forth in claim 1, wherein the electrolyte support has an annular groove with a diameter less than a diameter of the protruding annular section; and the lateral channel connects with said groove and extends outwardly from such groove.

6. An electrolyte housing as set forth in claim 5, wherein the annular groove is spaced from an electrode by an annular section having a roughening substantially shallower than the annular groove.

* * * * *